United States Patent [19]

Goldberg et al.

[11] Patent Number: 5,656,443

[45] Date of Patent: Aug. 12, 1997

[54] METHOD OF DIAGNOSING BLADDER CANCER

[75] Inventors: Itzhak D. Goldberg, Engelwood, N.J.; Eliot M. Rosen; Gary H. Weiss, both of Port Washington, N.Y.

[73] Assignee: Long Island Jewish Medical Center, New Hyde Park, N.Y.

[21] Appl. No.: 282,198

[22] Filed: Jul. 29, 1994

[51] Int. Cl.⁶ .................................................. G01N 33/574
[52] U.S. Cl. ................................................ 435/7.23; 436/64
[58] Field of Search ................................. 435/7.23; 436/64

[56] References Cited

U.S. PATENT DOCUMENTS

| 4,447,545 | 5/1984 | DeFazio et al. | 436/518 |
| 5,362,716 | 11/1994 | Kmiecik et al. | 514/12 |

OTHER PUBLICATIONS

Chodak et al. "Urine from Patients with Transitional–cell carcinoma stimulates migragtion of capillary endothelial cells", The New England Journal of Medicine, vol. 305, No. 15, pp. 869–874, issued 08 Oct. 1981.

Yamashita et al. "Immunoreactive Hepatocyte Growth Factor is a strong and Independent Predictor of Recurrence and Survival in Human Breast Cancer", Cancer Research, vol. 54, pp. 1630–1633, issued 01 Apr. 1994.

*Primary Examiner*—Toni R. Scheiner
*Assistant Examiner*—Yvonne Eyler
*Attorney, Agent, or Firm*—Amster, Rothstein & Ebenstein

[57] ABSTRACT

This invention relates to a method of diagnosing and screening for transitional cell carcinoma of the bladder. Urine from an individual suspected of having transitional cell carcinoma of the bladder is analyzed for the presence of an increased level of scatter factor, an increased level of scatter factor indicating that said individual has bladder cancer. This invention further relates to a method of monitoring bladder cancer activity by measuring the level of scatter factor in urine, and to a method of determining the prognosis of an individual having bladder cancer by measuring the level of scatter factor in tumor extract from the individual.

6 Claims, 8 Drawing Sheets

METHOD OF DIAGNOSING BLADDER CANCER

FIELD OF THE INVENTION

This invention relates to a method of diagnosing bladder cancer. Specifically, this invention is directed to a method of diagnosing and screening for transitional cell carcinoma of the bladder, to a method for monitoring the course of bladder cancer and to a method of determining the prognosis of an individual having transitional cell carcinoma of the bladder.

BACKGROUND OF THE INVENTION

Carcinoma is a malignant epithelial neoplasm which invades surrounding tissue and metastasizes to distant regions of the body. Transitional cell carcinoma is a malignant, usually papillary tumor derived from transitional stratified epithelium, which occurs most frequently in the bladder. Most tumors in the collecting system of the human body are transitional cell carcinomas.

In order to diagnose transitional cell carcinoma in the bladder, it is necessary to do a biopsy. A biopsy is the removal of a small sample of living tissue from an organ, such as the bladder, for microscopic examination to confirm or establish a diagnosis, estimate prognosis, or follow the course of a disease. Biopsies are invasive procedures, and are therefore not desirable as it is necessary for a person undergoing biopsy to undergo anesthesia. In addition, as with any invasive procedure, an individual undergoing biopsy runs the risk of infection. Further, the entire bladder cannot be biopsied to determine whether bladder cancer is present. Biopsy procedures often require individuals to be admitted into hospitals. Alternatively, urinary cytology analysis can be performed to diagnose transitional cell carcinoma of the bladder. However, urinary cytology analysis is a time-consuming procedure, which is not always accurate. Therefore, a need exists to develop a method of diagnosing and screening for carcinoma, including transitional cell carcinoma of the bladder, as well as for monitoring cancer activity and determining the prognosis of an individual having bladder cancer.

Scatter factor has previously been described as a cytokine which is secreted by fibroblasts (see Stoker et al., *J. Cell Sci.*, Vol. 77, pp. 209–223 (1985) and Stoker et al., *Nature* (London), Vol. 327, pp. 238–242 (1987)) and by vascular smooth muscle cells (see Rosen et al., *In Vitro Cell Dev. Biol.*, Vol. 25, pp. 163–173 (1989)). Scatter factor has been shown to disperse cohesive epithelial colonies and stimulate cell motility, proliferation and morphogenesis. In addition, scatter factor has been shown to be identical to hepatocyte growth factor (HGF) (see Weidner et al., *Proc. Nat'l. Acad. Sci. USA*, Vol. 88, pp. 7001–7005 (1991) and Bhargava et al., *Cell Growth Differ.*, Vol. 3, pp. 11–20 (1992)), which is an independently characterized serum mitogen (see Miyazawa et al., *Biochem. Biophys. Res. Commun.*, Vol. 169, pp. 967–973 (1989) and Nakamura et al., *Nature* (London), Vol. 342, pp. 440–443 (1989)). Scatter factor induces kidney epithelial cells in a collagen matrix to form branching networks of tubules, suggesting that it can also act as a morphogen (see Montesano et al., *Cell*, Vol. 67, pp. 901–908 (1991)).

Scatter factor (HGF) is a basic heparin-binding glycoprotein consisting of a heavy (58 kDa) and a light (31 kDa) subunit. It has 38% amino acid sequence identity with the proenzyme plasminogen (see Nakamura et al., *Nature* (London), Vol. 342, pp. 440–443 (1989)) and is thus related to the blood coagulation family of proteases. Its receptor in epithelium has been identified as the c-met proto-oncogene product, a transmembrane tyrosine kinase (see Bottaro et al., *Science*, Vol. 251, pp. 802–804 (1991) and Naldini et al., *Oncogene*, Vol. 6, pp. 501–504 (1991)).

Scatter factor has been found to stimulate endothelial chemotactic and random migration in Boyden chambers (see Rosen et al., *Proc. Soc. Exp. Biol. Med.*, Vol. 195, pp. 34–43 (1990)); migration from carrier beads to flat surfaces (see Rosen et al., *Proc. Soc. Exp. Biol. Med.*, Vol. 195, pp. 34–43 (1990)); formation of capillary-like tubes (see Rosen et al., *Cell Motility Factors*, (Birkhauser, Basel) pp. 76–88 (1991)) and DNA synthesis (see Rubin et al., *Proc. Nat'l. Acad. Sci. USA*, Vol. 88, pp. 415–419 (1991)). In addition, preliminary studies have suggested that scatter factor induces endothelial secretion of plasminogen activators (see Rosen et al., *Cell Motility Factors*, (Birkhauser, Basel) pp. 76–88 (1991)).

Structurally, scatter factor is not related to the classic growth factors but is a member of the family of kringle-containing proteins. This family is characterized by triple disulfide loop structures (kringles) that mediate protein:protein and protein:cell interactions. Other kringle proteins include plasminogen, prothrombin, urokinase, and macrophage-stimulting protein. Although scatter factor is structurally related to plasminogen, it lacks proteolytic activity because of two amino acid substitutions at the catalytic center of its β-chain.

Scatter factor disrupts intercellular junctions and stimulates random motility, directed migration, invasion, and production of proteases required for invasion in various human carcinoma cell lines. The inventors determined that scatter factor switches on a program of cellular activities for carcinoma-related activities. Further, scatter factor is a very potent inducer of angiogenesis, a process required for tumor growth and dissemination.

It is therefore an object of this invention to provide a method of diagnosing transitional cell carcinoma of the bladder by determining the level of scatter factor in the urine of an individual.

It is another object of this invention to provide a method of screening for transitional cell carcinoma of the bladder by determining the level of scatter factor in the urine of an individual.

It is yet another object of this invention to provide a method of monitoring the course of bladder cancer in an individual having bladder cancer by determining the level of scatter factor in the urine of said individual.

It is a further object of this invention to provide a method of determining the prognosis of an individual having bladder cancer by determining the level of scatter factor in tumor extracts from said individual.

SUMMARY OF THE INVENTION

This invention is directed to a method of diagnosing bladder cancer in an individual suspected of having bladder cancer and to a method of screening for bladder cancer. In order to screen or diagnose bladder cancer, urine from an individual is analyzed for the presence of a high level of scatter factor, a high level of scatter factor in the urine indicating that said individual has bladder cancer.

This invention is further directed to a method of monitoring the course of bladder cancer in an individual comprising analyzing urine from said individual for the presence of an increased level of scatter factor, an increased level of scatter factor in the urine indicating a high level of bladder cancer activity.

This invention is also directed to a method of determining the prognosis of an individual having bladder cancer comprising determining whether there is an increased level of scatter factor present in tumor extract from said individual, an increased level of scatter factor correlating with a poor prognosis for said individual.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein.

DETAILED DESCRIPTION OF THE INVENTION

In the following tests, scatter factor was measured using an ELISA. In order to perform the ELISA, immunoreactive scatter factor protein was measured using a double antibody (sandwich) ELISA. Immulon II 96-well plates (Dynatech) were coated with anti-human scatter factor mouse monoclonal 23C2 ascites (see Bhargava et al., *Cell Growth Differen.*, Vol. 3, pp. 11–20 (1992)) (1:1000) in 0.1M $Na_2CO_3$ buffer, pH 9.6, overnight at 4° C. (100 µl/well). Wells were washed 4 times with tris-buffered saline (20 mM tris, 150 mM NaCl, 0.05% Tween-20, pH 7.5) (TBS), blocked with 0.5% gelatin in TBS for 1 hour at 37° C., washed 4 times, incubated for 1 hour at 37° C. with 100 µl of test sample or standard (recombinant human scatter factor, Genentech); and re-washed. Wells were then incubated with sheep anti-scatter factor antiserum (Genentech) (1:2000) for 1 hour at 37° C. in 0.25% gelatin in TBS, washed 4 times, incubated with goat anti-sheep IgG conjugated to alkaline phosphatase (50 µg/ml) (1 hour at 37° C.) to recognize bound anti-scatter factor antibody; and washed again. Color was developed by incubation with 100 µl of substrate solution [p-nitro phenyl phosphate (1 mg/ml), 1M diethanolamine HCl, 2 mM $MgCl_2$, pH 9.8]. The reaction was stopped by adding 50 µl of 3M NaOH, and absorbance was read at 410 nm using a Dynatech multiwell spectrophotometer. The assay was specific for scatter factor. It did not detect plasminogen, albumin, or various growth factors and cytokines. The linear measuring range was about 0.2–4.0 ng/ml of scatter factor. Samples were diluted so that scatter factor concentrations fell in this range.

Scatter factor activity was quantitated using the MDCK serial dilution scatter assay, a sensitive and specific bioassay for scatter factor (see Bhargava et al. (1992) and Rosen et al., *Proc. Soc. Exp. Biol Med.*, Vol. 195, pp. 34–43 (1990)). The scatter factor concentration at the limiting dilution was defined as 0.5 MDCK scatter units/ml, allowing calculation of the scatter factor titer in the original sample.

In order to perform Northern blotting, confluent MRC5 fibroblast cultures were incubated for 24 hours in serum-free DMEM (10 ml per 100 mm dish) containing 25 µl of tissue extract. The total cell RNA was isolated by acid guanidinium isothiocyanate-phenol-chloroform extraction (see Chomczynski et al., *Anal. Biochem.*, Vol. 162, pp. 156–159 (1987)). Equal aliquots of RNA (30 µg) from each experimental condition were electrophoresed through 1% agarose-17% formaldehyde gels. Northern transfers and hybridization were performed as described by Elias et al., *J. Immunol.*, Vol. 145, pp. 161–166 (1990). Membranes were probed with a 2.2 kb insert containing the complete human HGF cDNA subcloned into the Sal 1 restriction site of the pUC vector. (The insert was subcloned from the ENC-hHGF construct (see Nakamura et al., *Nature*, Vol. 342, pp. 440–443 (1989)), which was provided by Dr. T. Nakamura). Sizes of transcripts were assessed by comparison to RNA size standards (BioRad, Richmond, Va.). To control for loading and transfer, the blot was stripped and re-probed using a cDNA coding for β-actin. cDNA probes were labelled by nick translation to specific activities of about $10°$ CPM/µg DNA. Membranes were washed with 0.5× SSC containing 0.1% SDS for 30 minutes at 50° C., and autoradiography was performed.

In order to perform Western blotting of scatter factor, samples were mixed with Laemmli sample buffer without mercaptoethanol and analyzed on a 12% SDS-polyacrylamide gel. Immunoblotting was performed as described before by Bhargava et al., (1992). The primary antibody, rabbit polyclonal antiserum against native human placental scatter factor (Ab978), was used at a 1:4000 dilution. Identical results were obtained using either of two mouse monoclonal antibodies (23C2 or 10C11) Bhargava et al., (1992) against human scatter factor. Bound primary antibody was recognized using the enhanced chemiluminescence (ECL) detection system (Amersham).

Urine samples were tested for the presence of scatter factor. Urine was collected from patients evaluated in the Urology Department, Long Island Jewish Medical Center, New York. These patients had not had either recent bladder instrumentation or urinary tract infection. Samples were stored frozen at –20° C. prior to processing. Samples were centrifuged to remove the sediment and concentrated (30–50)-fold using an Amicon YM-30 (30 kDa) ultrafiltration membrane. The >30 kDa retentate was assayed for scatter factor content by ELISA. A portion of the original (unconcentrated) urine specimen was assayed for creatinine by the Clinical Chemistry Laboratory at Long Island Jewish Medical Center (LIJMC). The scatter factor content of the urine was expressed as pg of scatter factor per mg of creatinine.

Figure 1:
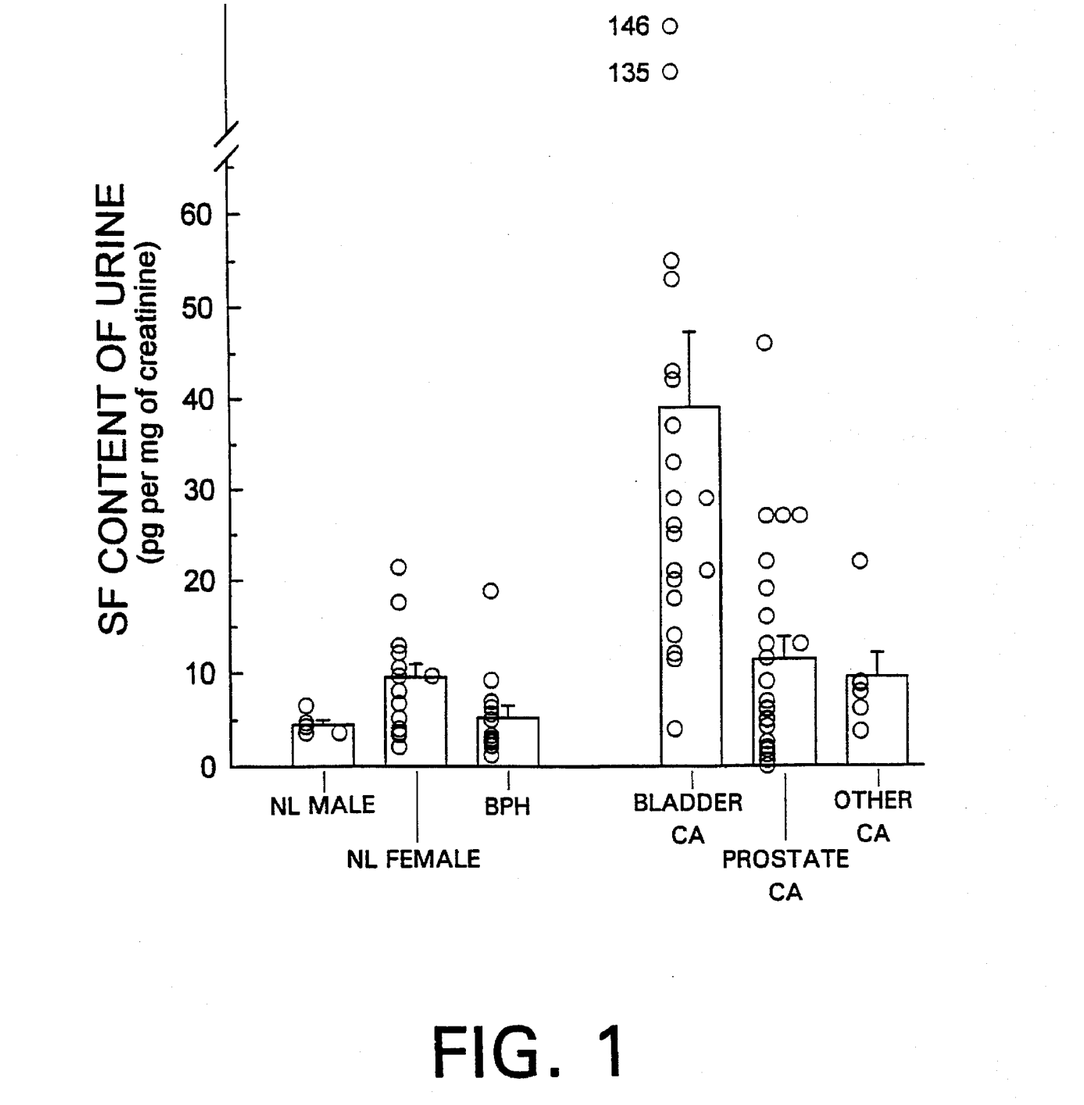
FIG. 1 represents the quantitation of scatter factor in the urine of normal individuals, individuals with bladder carcinoma and individuals with prostate carcinoma and benign prostatic hypertrophy.
Figure 2:
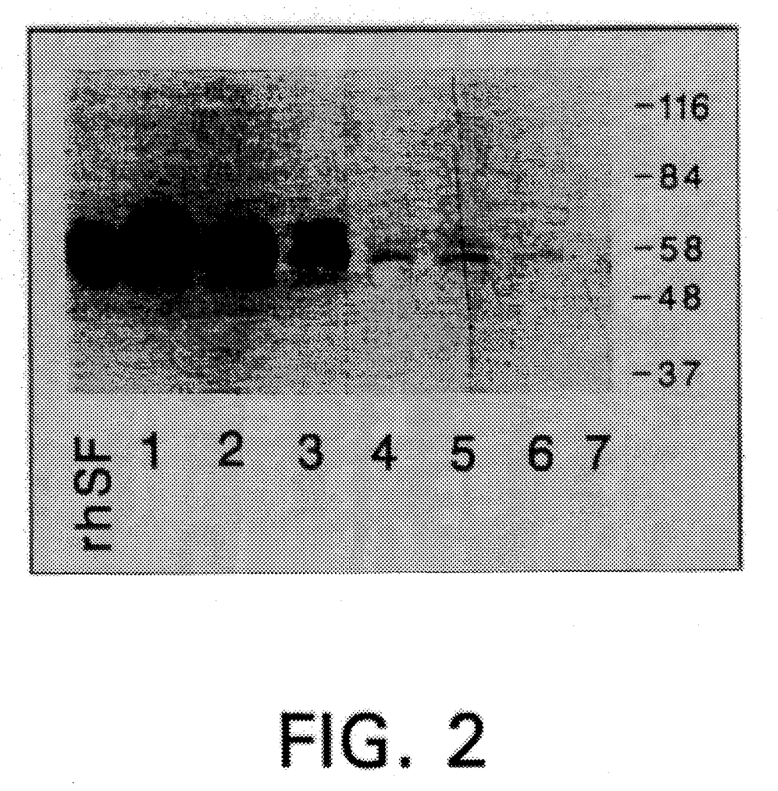
FIG. 2 represents a Western blot of concentrated urine from patients with transitional cell carcinoma of the bladder and from normal individuals.
Figure 3A:
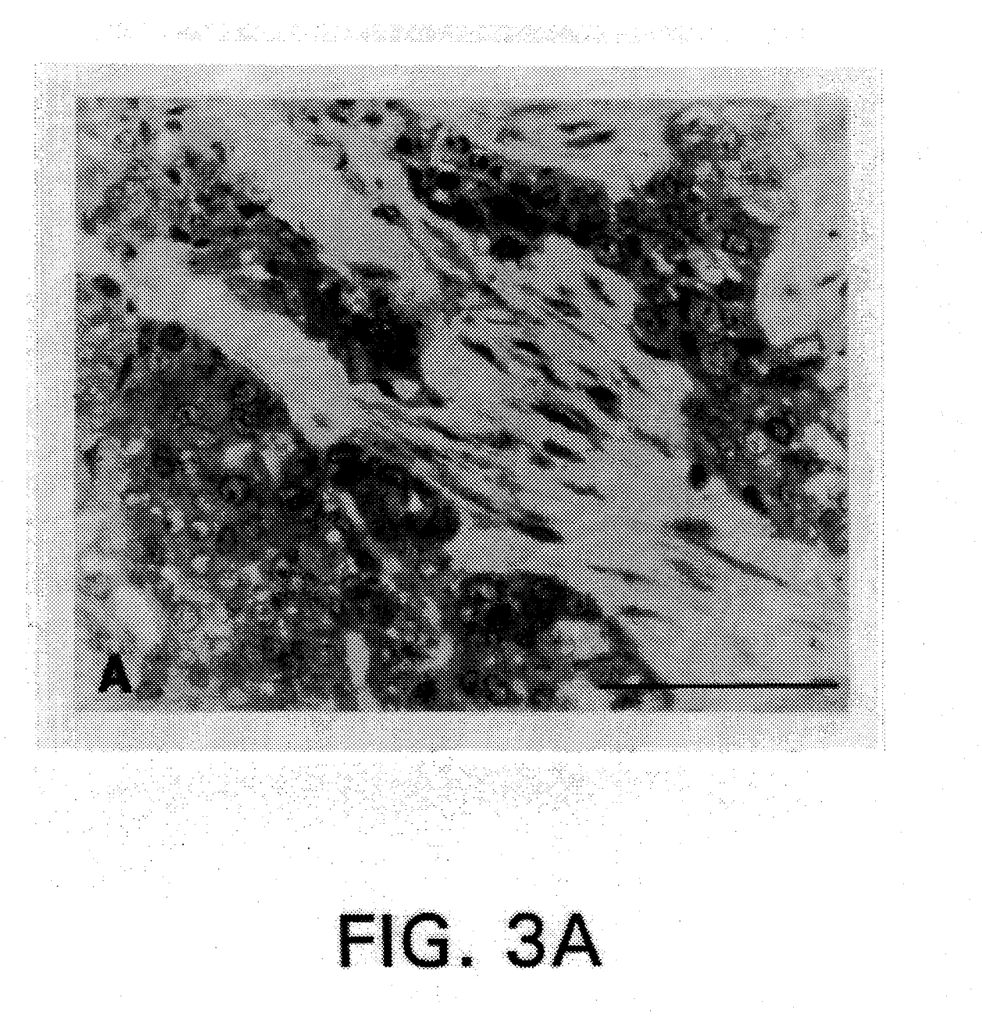
FIG. 3 represents an immunoperoxidase staining of human transitional cell bladder carcinoma sections.
Figure 3B:
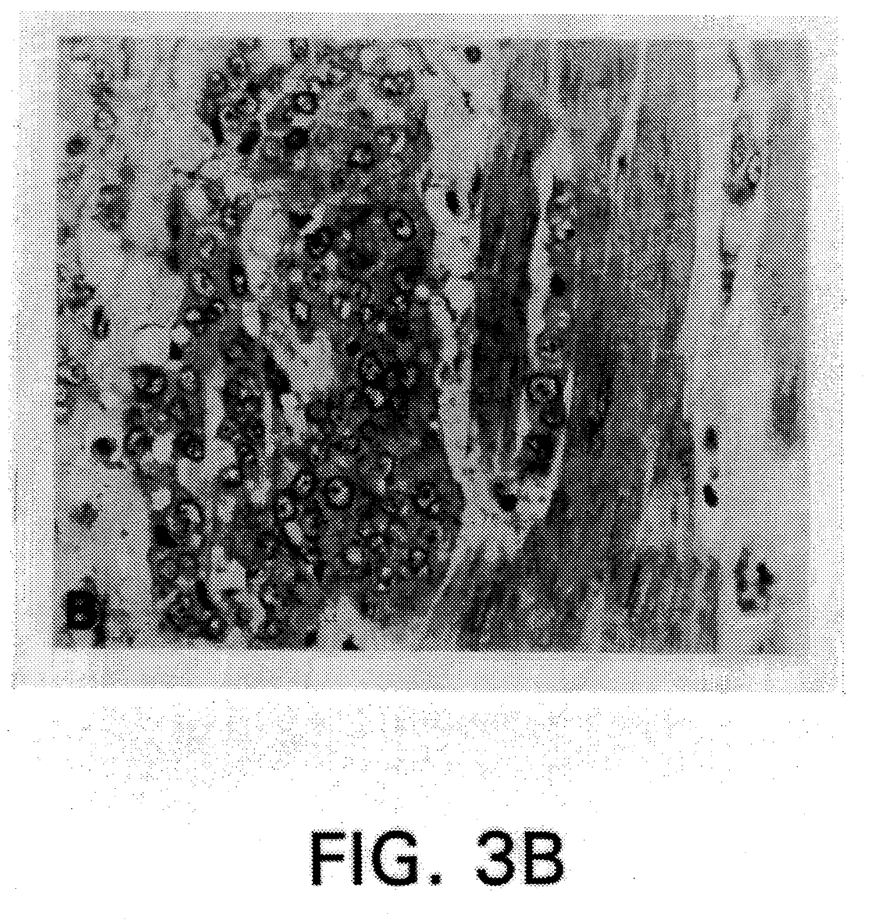
Figure 3C:
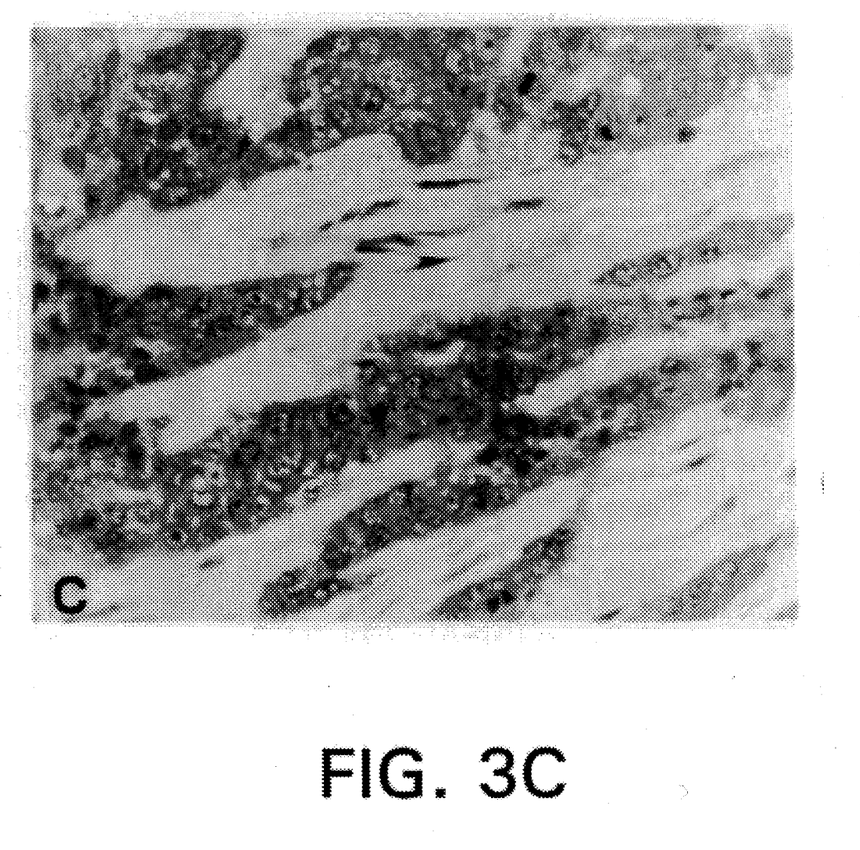
Figure 3D:
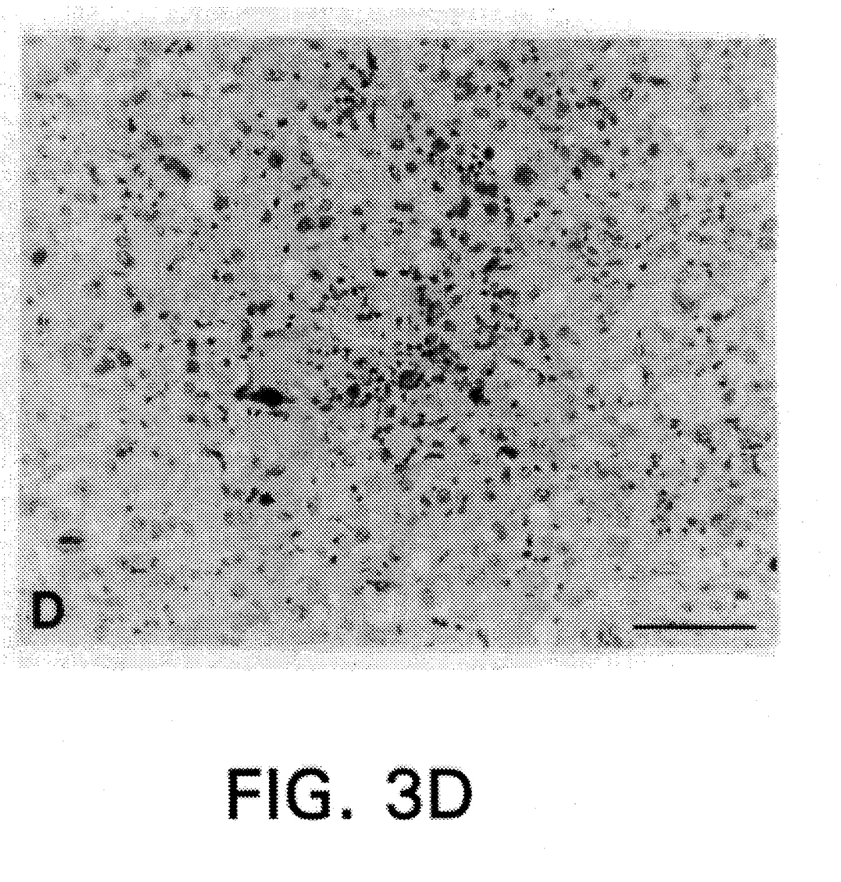

Scatter factor in the urine of bladder cancer patients was quantified using the previously described ELISA. It was found that the mean scatter factor titer in urine from 20 patients with bladder cancer (39.0±8.3 pg scatter factor/mg creatinine) was significantly greater than those from normal controls, patients with benign prostatic hypertrophy (BPH), and patients with other tumors affecting the genitourinary system (FIG. 1). The presence of authentic, high molecular weight scatter factor in urine from bladder cancer patients was verified by Western blotting, which revealed increased scatter factor in urine from three bladder cancer patients as compared with four normal controls (FIG. 2). The scatter factor in urine was biologically active.

Patients with biopsy-documented BPH showed similar urinary scatter factor levels [5.2±1.3 (N=13)] to normal males [4.5±0.5 (N=5)]. BPH patients were an appropriate control group, since these patients were older men about the same age as the bladder cancer patients (85% male). Urinary scatter factor was significantly elevated in patients with benign inflammation of the prostate [20.8±2.7 (N=5)] as compared with BPH (P<0.001). These patients were diagnosed as having prostatitis, inflammatory giant cell prostatitis, or chronic granulomatous prostatitis based on prostate biopsy.

Although some patients with prostate carcinoma had slightly elevated scatter factor levels, the mean value for prostate cancer [11.4±2.4 pg scatter factor/mg creatinine (N=23)] was lower than for bladder cancer patients (P=0.002). Sixteen of 20 patients (80%) with bladder cancer had urinary scatter factor titers >15, whereas 7/23 patients (30%) with prostate cancer, and 3/33 controls (nl male/nl female/BPH) (9%) had scatter factor titers >15 pg scatter factor/mg creatinine. No control or BPH patients had urinary scatter factor titers >21, while 13/20 bladder cancer patients (65%) had titers >21. Urine from patients with other types of cancers that were evaluated in the Urology Department of LIJMC for problems relating to the urinary system (e.g., ureteral obstruction) was assayed in the ELISA. The diagnosis and scatter factor values were as follows: metastatic lung cancer (3.7), colon cancer (7.9), ovary cancer (6.1), verrucous cancer of cervix and vagina (8.7), squamous cancer of the penis (8.9), and retroperitoneal B cell lymphoma (22 pg scatter factor/mg creatinine). Thus, cancer involving the genitourinary system other than the bladder is not associated with elevated urinary scatter factor.

A urine sample from a patient that was disease-free 4.5 months after radical nephrectomy for renal carcinoma was assayed in the ELISA. This urine had an scatter factor content of 167 pg/mg creatinine, the highest value of any urine tested. Following unilateral nephrectomy, scatter factor production in the remaining kidney and in distant organs is stimulated. This very high urine scatter factor level may reflect excess production of scatter factor due to the trauma of major surgery and/or the compensatory hyperplastic response.

FIG. 1 shows the urinary scatter factor content for different groups of patients. The scatter factor content was determined by ELISA as previously described herein. Each data point represents a different patient. Where serial urines were available, the average value was used, and variations were small, except in one case. For this patient, marked elevation of urinary scatter factor corresponded to biopsy-proven recurrence of bladder tumor. Bars show mean values for each group of patients±standard errors. Bladder carcinoma patients were compared to other groups of patients using two-tailed t-tests: normal controls, P<0.001; prostate carcinoma, P=0.002; BPH (benign prostate hypertrophy), P=0.0055; other cancers, P=0.072.

FIG. 2 shows detection of urinary scatter factor by Western blotting. Aliquots of concentrated urine equalized by protein content (30 µg per lane) were blotted to detect scatter factor. Lanes 1–3 show urine samples from three patients with transitional cell carcinoma of bladder, and lanes 4–7 show samples from four normal controls. Recombinant human scatter factor (rhSF) was used as a positive control.

Scatter factor-inducing activity was then detected in urine. The ability of urine concentrates from transitional cell carcinoma patients vs. controls to stimulate scatter factor production by MRC5 cells were compared. Four patients with active transitional cell carcinoma and elevated urinary scatter factor were studied. Controls included two patients with BPH and two patients with prostate carcinoma that had normal urinary scatter factor. The amount of concentrate added was normalized according to the original (pre-filtration) creatinine content (0.2 or 0.4 mg creatinine). The MRC5 scatter factor production rates (ng/$10^6$ cells/24 hours) were: no addition, 5.2±1.2; control patients, 6.9±1.0 (0.2 mg creatinine) and 7.6±1.1 (0.4 mg); transitional cell carcinoma patients, 20.1±3.0 (0.2 mg) and 22.6±1.8 (0.4 mg).

Based on dose response studies, urine from transitional cell carcinoma patients contained 20–100 scatter factor-inducing activity units/mg creatinine. Similar to the findings with transitional cell carcinoma culture medium, the <30 kDa filtrate of urine contained little or no scatter factor-inducing activity, and the >30 kDa urinary scatter factor-inducing activity was destroyed by heating. Although the urine from the transitional cell carcinoma patients contained detectable amounts of scatter factor, the samples were diluted >20-fold in the assays, to a concentration that was too small to detect. Thus, scatter factor added to the assay could not have influenced the findings.

The presence of scatter factor in bladder tumor extracts was determined. Bladder tissue was snap frozen and stored at −80° C. To prepare extracts, tissues were thawed, washed, cut into small pieces and homogenized in extraction buffer (20 mM Tris, pH 7.5, 0.5M NaCl, 0.1% EDTA, 0.1 mM PMSF, 5 µg/ml leupeptin) (4 ml/g of tissue). The homogenized tissue was sonicated and then clarified by microfuging. The precipitate was re-extracted using the same buffer containing a higher salt concentration (1M NaCl). The high salt extractions were used to extract scatter factor bound to heparin sulfate proteoglycans in the matrix and on the cell surface. Experiments showed that a third extraction did not yield additional scatter factor. The two clarified supernatants were pooled and the excess salt was removed by dialysis. Dialyzed extracts were assayed for scatter factor by ELISA and for protein using the BioRad Coomassie blue dye-binding assay.

In order to quantify scatter factor in bladder tumor extracts, the bladder tumor extracts from twelve patients were assayed for scatter factor content by ELISA. High titers of scatter factor were detected in all samples, with a mean value of 2.80±0.85 ng of scatter factor/mg of protein (range 0.42–10.3) or 167±37 ng of scatter factor/g of tissue (range 25–394). Extracts from high grade (III-IV), invasive carcinomas showed higher scatter factor content [3.62±0.90 ng/mg of protein (N=7)] than did extracts from low grade (I-II), superficial tumors [0.83±0.24 ng/mg of protein (N-4)] (P=0.05, two-tailed t-test), with the exception of one low grade recurrence of a previously invasive carcinoma (5.0 ng/mg).

Scatter factor was assayed for in normal muscle (rectus abdominus), bladder tissue peripheral to the tumor, and bladder tumor from a patient who had undergone radical cystectomy for high grade, invasive transitional cell carcinoma. Levels of scatter factor were markedly higher in the tumor (4.0) than in the peripheral bladder (0.32) or muscle (0.12 ng/mg). Tissue extracts contained biologically active scatter factor, as demonstrated using the MDCK scatter assay. In addition, Western blots revealed authentic high molecular weight scatter factor.

In order to perform immunohistochemistry procedures on the tumor extracts, four-micrometer thick paraffin sections from high grade (III or IV) human transitional cell bladder carcinomas were de-waxed using standard techniques. Sections were stained using a Vectastain ABC immunoperoxidase kit (Vector Laboratories, Burlington, Vt.) and counterstained with hematoxylin. The primary antibody was rabbit antiserum against native human placental scatter factor (Ab978) (1:200) (see Bhargava et al. (1992)), rabbit antiserum against a C-terminal 28 amino acid c-met peptide (AbC28) (1:500) (see Bottaro et al., *Science*, Vol. 251, pp. 802–804 (1991)), or rabbit non-immune serum (1:200) (negative control). As additional controls, anti-scatter factor Ab978 (1:200) or anti-c-met AbC28 (1:500) which had been pre-incubated with recombinant human scatter factor (5 μg/ml) or c-met C28 peptide (10 μg/ml), respectively, were used as the primary antibodies. The intensity of staining was scored semi-quantitatively, as follows: 0 (no staining), 1+ (definite), 2+ (strong), 3+ (very strong) staining.

Scatter factor and c-met, the oncogene which encodes scatter factor receptor were detected by immunohistochemistry. Samples of transitional cell carcinoma tumor tissue from four patients with grade III-IV muscle-invasive tumors were immunostained for scatter factor and for c-met protein. In all four tumors, transitional cell carcinoma tumor cells stained strongly (2+ to 3+) for both scatter factor and c-met (see FIG. 3). Strongly positive staining for scatter factor was observed with rabbit polyclonal antiserum (Ab978) and with anti-scatter factor mouse monoclonals 23C2 and 10C11 [1:500 of ascites].

Antigen competition controls (i.e., pre-incubation of antibody with purified antigen) gave easily visible reduction in staining for both scatter factor and c-met, verifying the specificity of the reaction. In addition to tumor cells, grossly normal epithelium adjacent to invasive carcinoma stained positively for scatter factor and c-met. Positive staining for scatter factor and c-met was also observed in non-epithelial cell types, including microvascular (capillary and venular) endothelial cells, and bladder wall smooth muscle cells (see FIG. 3B). Staining of these cell types was more variable and was often lower in intensity (1+ to 2+).

FIG. 3 shows immunoperoxidase staining of human transitional cell bladder carcinoma sections. Four-μm thick paraffin sections were stained using rabbit antiserum against scatter factor (Ab978) (FIG. 3, panels A and B), rabbit anti-c-met AbC28 (FIG. 3, panel C), and rabbit non-immune serum (negative control) (FIG. 3, panel D) as the primary antibodies. Panels A and B show sections from two different tumors. Stained sections were photographed under the same illumination and printed using the same filtration. The bar represents 100 μm.

Scatter factor-inducing activity (scatter factor production by fibroblasts) in tissue extracts was detected. In order to do this, extracts of normal muscle (rectus abdominus), bladder tissue peripheral to the tumor, and bladder tumor from the same patient with invasive transitional cell carcinoma were assayed for scatter factor-inducing activity. Production of scatter factor by MRC5 was stimulated to a greater extent by the tumor extract than by the non-tumor extracts, as demonstrated by bioassay, ELISA, Western blotting (FIG. 4, panel C), and Northern blotting (FIG. 4, panel D). The increase in the scatter factor content of the MRC5 culture medium was not due to the scatter factor present in the tumor extract since: (1) the concentration of extract (24 μl in 10 ml of DMEM) was too low to detect scatter factor by bioassay, ELISA, or Western blotting (FIG. 4, panel C); and (2) bladder tumor extract clearly stimulated scatter factor mRNA expression (FIG. 4, panel D).

Extract from bladder tissue peripheral to the main tumor mass did stimulate MRC5 scatter factor protein production. This tissue may have contained carcinoma-in-situ or dysplastic epithelium that appeared grossly normal. Based on the scatter factor ELISA, the tumor extract contained >400 scatter factor-inducing activity units/g of tissue.

FIG. 4, panel C shows the detection of scatter factor-inducing activity in bladder tissue extracts. Confluent MRC5 cells in 100 mm dishes were incubated for 24 hours in 10 ml of DMEM with no addition (control), peripheral bladder tissue extract (25 μl) were blotted to detect scatter factor. Lanes 1 and 2 are controls in which fresh DMEM (10 ml) plus extract (25 μl) were concentrated and blotted (1=peripheral bladder, 2=tumor). Lanes 3, 4, and 5 represent media from cells incubated with no addition, peripheral bladder, and tumor, respectively. The lanes to the left of lane 1 contained rhSF (50 ng) and HPSF (50 ng) (positive controls).

FIG. 4, panel D shows the detection of scatter factor-inducing activity in tissue extracts by Northern blotting. MRC5 cells were treated without or with extract (25 μl), and Northern blotting was performed as described herein. The top panel shows the expression of the 6 kb scatter factor mRNA. The bottom panel shows expression of the 2.5 kb β-actin mRNA. Lane 1=no addition (control), lane 2=normal muscle (rectus abdominus), 3=peripheral bladder tissue, and 4=bladder tumor.

In the following tests, cell types and culture were obtained as follows: MRC5 human lung fibroblasts, human bladder carcinoma cell lines (RT4, HT1197 and SCaBER), and human glioma cells (U87MG) were obtained from the American Type Culture Collection, Rockville, Md. Madin-Darby canine kidney (MDCK) epithelial cells were obtained from Dr. Stephen Warren (Department of Pathology, Yale University School of Medicine). Cells were grown in Dulbecco's Modified Eagle's Medium (DMEM) supplemented with 10% (v/v) fetal calf serum, 0.1 mM non-essential amino acids, penicillin (100 U/ml), and streptomycin (100 μg/ml), and subcultured as described earlier by Rosen et al., *Proc. Soc. Exp. Biol. Med.*, Vol. 195, pp. 34–43 (1990).

In order to characterize scatter factor-inducing activity in tumor cell culture medium, tumor cell culture medium was ultrafiltered using an Amicon YM-30 membrane, boiled (100° C. for 5 minutes), or treated with trypsin. To determine the effect of trypsin on scatter factor-inducing activity, culture medium was incubated with bovine trypsin (Sigma Chemical Co., St. Louis, Mo.) (50 μg/ml) for 30 minutes at 37° C. and then soybean trypsin inhibitor (100 μg/ml) was added. For the control, soybean trypsin inhibitor was added before trypsin. The scatter factor-inducing activity (units/ml) was quantitated and compared with the control value.

Production of scatter factor-inducing activity by cultured human TCC cells was determined. Culture medium from three lines of human transitional cell carcinoma, RT4 (derived from a recurrent, well-differentiated tumor), HT1197 (derived from a poorly-differentiated tumor), and SCaBER (derived from a transitional cell carcinoma with squamous metaplasia) were assayed for their ability to stimulate scatter factor production by human fibroblasts (MRC5) and glial cells (U87MG).

None of the tumor cell culture medium samples contained any detectable scatter factor by ELISA or bioassay. However, cm from all three lines contained significant scatter factor-inducing activity for MRC5 and U87MG cells (see FIGS. 4A and 4B). The maximum rates of scatter factor production were 3–4 times the control values. The doubling doses (i.e., the percentages of culture medium required to double the scatter factor production rate) were in the range of 2–10% (v/v). The titers of scatter factor-inducing activity in the culture medium were 26, 59, and 25 units/ml for RT4, HT1197, and SCaBER cells, respectively.

The corresponding normalized rates of production of inducing activity were 4, 30, and 13 units/$10^6$ cells/24 hours. Corresponding increases in expression of scatter factor mRNA were observed in MRC5 cells treated with human transitional cell carcinoma culture medium. Fractionation of the culture medium by ultrafiltration revealed that the >30 kDa retentate contained the large majority of the scatter factor-inducing activity (see FIG. 4B). The >30 kDa scatter factor-inducing activity was destroyed by boiling (see FIG. 4A) and by treatment with trypsin, indicating that the activity is proteinaceous in nature.

Cell conditioned medium (CM) was assayed for scatter factor-inducing activity. To generate culture medium, confluent cultures of tumor cells were washed three times and incubated in serum-free DMEM (0.1 ml per $cm^2$) for 48 hours. The medium was centrifuged to remove debris (3000 RPM×20 min) and stored at −20° C. To determine if the culture medium contained scatter factor-inducing activity, the ability of the culture medium to stimulate scatter factor production by MRC5 fibroblasts was assessed as follows: Confluent MRC5 fibroblasts in 2-$cm^2$ culture wells were washed and incubated in 0.5 ml of serum-free DMEM containing various dilutions of culture medium for 24 hours. The resulting media were collected and centrifuged to remove debris, and the cells were counted. Scatter factor was quantitated by ELISA.

The scatter factor production rate was expressed as ng of scatter factor per $10^6$ cells per 24 hours. For each assay condition, duplicate determinations of scatter factor production were made. Each experiment was performed at least three times. To quantitate scatter factor-inducing activity one scatter factor-inducing activity unit/ml was defined as the concentration of inducer required to double the rate of scatter factor production rate by MRC5 cells.

Figure 4A:
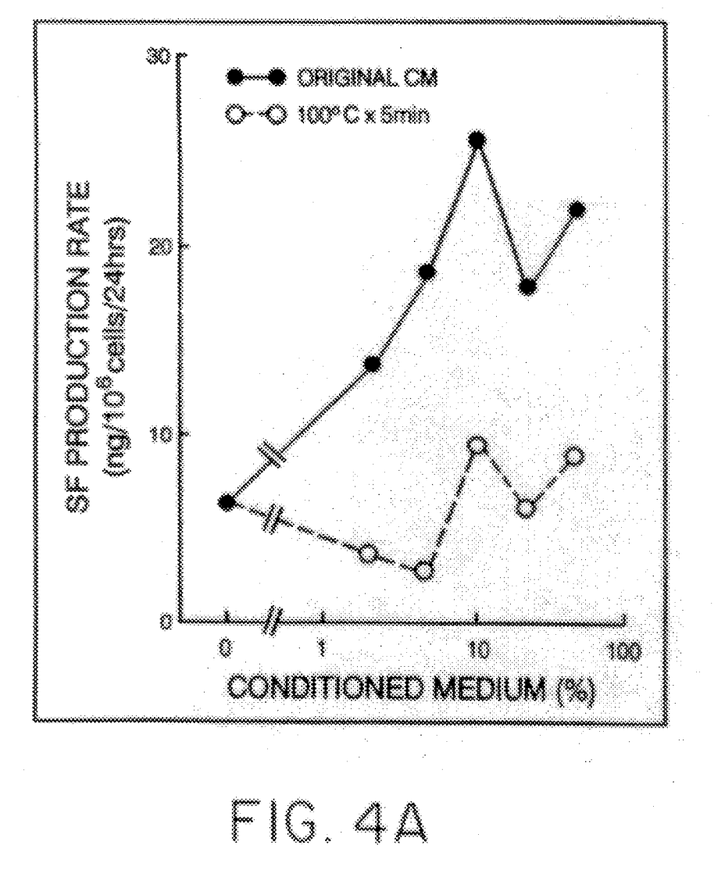
FIG. 4A represents a dose response for scatter factor-inducing activity in culture medium from a human bladder carcinoma cell line HT1197.

FIG. 4A shows dose response curve for scatter factor-inducing activity in CM from a human bladder carcinoma cell line (HT1197). As described, confluent MRC5 cells in 2-$cm^2$ wells were incubated for 24 hours in DMEM containing different dilutions of original or heated HT1197 culture medium. The resulting media were assayed for scatter factor by ELISA. Values are means of duplicate determinations, with a range fo ±5% of the mean.

Figure 4B:
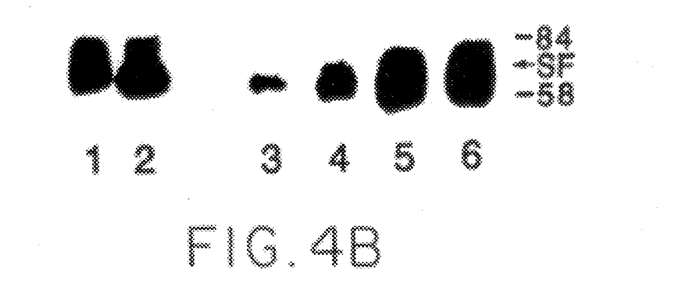
FIG. 4B represents a characterization of scatter factor-inducing activity in HT1197 culture medium by Western blot.
Figure 4C:
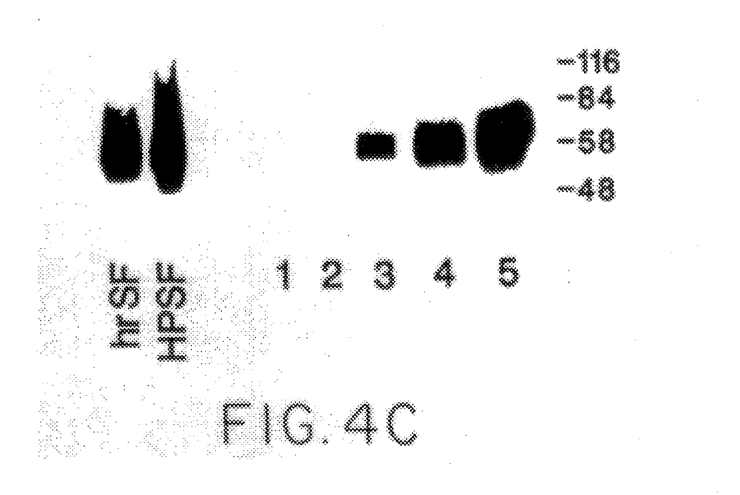
FIG. 4C represents the detection of scatter factor-inducing activity in bladder tissue extracts by Western blot.
Figure 4D:
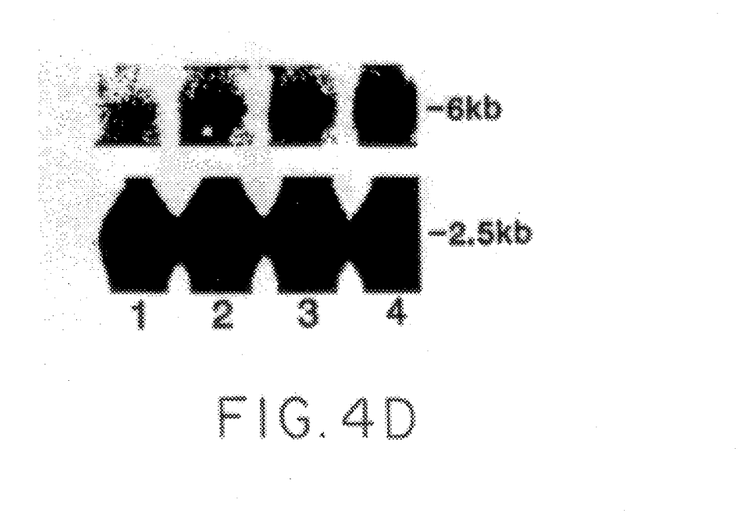
FIG. 4D represents the detection of scatter factor-inducing activity in tissue extracts by Northern blot.

FIG. 4B represents the characterization of scatter factor-inducing activity in HT1197 CM by Western blotting. Culture medium was fractionated using an Amicon membrane. Confluent MRC5 cultures in 100 mm dishes were incubated for 24 hours in 10 ml of DMEM without or with culture medium fractions [50% (v/v)]. The resulting media were concentrated 40-fold, and equal aliquots were blotted to detect scatter factor. Lanes 1 and 2 represent rhSF (25 ng) and native human placental scatter factor (HPSF, 50 ng) (positive controls). Lanes 3–6 represent concentrated MRC5 24 hour media: 3 =no addition (control), 4=<30 kDa fraction, 5=>30 kDa fraction and 6=original HT1197 culture medium.

As described above, there are high levels of scatter factor in the urine of patients with transitional cell carcinoma of the bladder. The urinary scatter factor content of bladder cancer patients was significantly greater than that of normal controls, patients with BPH, and patients with other types of genitourinary cancers. High titers of scatter factor were also detected in bladder tumor extracts, with the highest titers in extracts from high grade, muscle invasive tumors. High tumor grade and invasion of bladder wall muscle are associated with increased risk of local recurrence and distant metastases. Therefore, measurement of scatter factor in urine can be used as a diagnostic tool for bladder carcinoma, to screen for bladder cancer and to monitor the course of bladder cancer activity. A level of at least about 20 pM scatter factor per mg creatinine in urine indicates the presence bladder cancer. Measurement of scatter factor in tumor extract from bladder cancer patents can be used as a prognostic indicator for said patients. A level of at least about 3 ng scatter factor per mg tumor protein correlates with poor prognosis. Hence, high levels of scatter factor in urine indicates the presence of carcinoma in the bladder and a high level of cancer activity, and increased scatter factor in tumor extracts from bladder cancer patients correlates with poor prognosis for said patients.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method of screening for bladder cancer in an individual comprising determining the level of scatter factor present in urine of said individual, the presence of an increased level of scatter factor in said urine relative to a normal control is indicative that said individual may have bladder cancer.

2. The method of claim 1 wherein said bladder cancer is transitional cell carcinoma of the bladder.

3. The method of claim 1 wherein the level of scatter factor in the urine is determined by a method selected from the group consisting of ELISA, Western blotting, and serial dilution scatter assay.

4. A method of screening for bladder cancer in an individual comprising determining the level of scatter factor present in urine from said individual, the presence of a level of scatter factor of at least about 20 pM/mg creatinine in said urine being indicative that said individual may have bladder cancer.

5. The method of claim 4, wherein said bladder cancer is transitional cell carcinoma.

6. The method of claim 4, wherein said level of scatter factor in the tumor extract is determined by a method selected from the group consisting of ELISA, Western blotting and serial dilution scatter assay.

* * * * *